United States Patent [19]

Schaulin et al.

[11] Patent Number: 4,661,292

[45] Date of Patent: Apr. 28, 1987

[54] PROCESS FOR THE PREPARATION OF 1,4-DIAMINO-2,3-DICYANOANTHRAQUINONE

[75] Inventors: Rudolf Schaulin, Riehen; Maurice Grélat, Melide, both of Switzerland

[73] Assignee: Ciba-Geigy Corporation, Ardsley, N.Y.

[21] Appl. No.: 784,434

[22] Filed: Oct. 3, 1985

[30] Foreign Application Priority Data

Oct. 26, 1984 [CH] Switzerland ............... 5121/84

[51] Int. Cl.$^4$ ............... C07C 143/665; C07C 97/24
[52] U.S. Cl. ............................. 260/371; 260/378
[58] Field of Search ........................... 266/378, 371

[56] References Cited

U.S. PATENT DOCUMENTS

| | | | |
|---|---|---|---|
| 4,294,769 | 10/1981 | Kröck et al. | 260/378 |
| 4,299,771 | 11/1981 | Takeshita et al. | 260/378 |
| 4,422,973 | 12/1983 | Kröck et al. | 260/378 |

FOREIGN PATENT DOCUMENTS

| | | | |
|---|---|---|---|
| 0023645 | 2/1981 | European Pat. Off. | 260/378 |
| 1108704 | 6/1961 | Fed. Rep. of Germany | 260/378 |
| 1142174 | 7/1963 | Fed. Rep. of Germany | 260/371 |
| 1155786 | 4/1964 | Fed. Rep. of Germany | 260/371 |
| 2524748 | 12/1976 | Fed. Rep. of Germany | 260/378 |

*Primary Examiner*—Glennon H. Hollrah
*Assistant Examiner*—Raymond Covington
*Attorney, Agent, or Firm*—Joseph G. Kolodny

[57] ABSTRACT

The invention relates to a process for the preparation of 1,4-diamino-2,3-dicyanoanthraquinone, starting from 1,4-diaminoanthraquinones, or salts thereof, of the formula

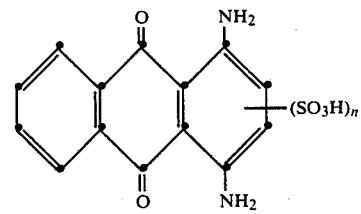

wherein n is 0, 1 or 2. To introduce the two cyanide radicals, the starting material is treated, in the presence of an oxidizing agent, with a compound which donates cyanide ions. The process comprises using as solvent a mixture of a carboxamide, an N-alkylated carboxamide or a lactam and water, which mixture contains more than 10% by weight of water.

1,4-Diamino-2,3-dicyanoanthraquinone is an important intermediate for the synthesis of textile dyes.

10 Claims, No Drawings

PROCESS FOR THE PREPARATION OF 1,4-DIAMINO-2,3-DICYANOANTHRAQUINONE

The present invention relates to a process for the preparation of 1,4-diamino-2,3-dicyanoanthraquinone, starting from 1,4-diaminoanthraquinone or 1,4-diaminoanthraquinonemono- or -disulfonic acid or salts thereof.

1,4-Diamino-2,3-dicyanoanthraquinone is an important intermediate for the synthesis of textile dyes. In the past, numerous processes for the preparation of diaminodicyanoanthraquinone have been developed. The starting material is usually 1,4-diaminoanthraquinone, 1,4-diaminoanthraquinone-2-sulfonic acid or 1,4-diamino-2,3-dihaloanthraquinones which are reacted with cyanides to give diaminodicyanoanthraquinone. The essential difference between these known processes resides in the nature of the solvent in which the reaction is carried out and in specific auxiliaries, where such are employed. As regards the solvent, the process is either carried out in water (e.g. German Auslegeschrift B-1 108 704) or under anhydrous conditions in an organic solvent (German Offenlegungsschrift A-25 24 748), or in formamide or N-methylformamide (published European patent application EP-A-23 645).

Both process variants have drawbacks. For example, the reaction in which water is used as reaction medium can only be carried out under very dilute conditions, resulting in a low space/time yield. On the other hand, the use of organic solvents makes it possible to carry out the reaction under highly concentrated conditions; but such procedures are rather troublesome, as not only the solvent but also the starting materials have to be dried prior to the reaction. In addition, the organic solvent has to be regenerated upon conclusion of the reaction.

It has now been found that the cyanation of diaminoanthraquinone or diaminoanthraquinonesulfonic acid can also be carried out in the presence of water when using a carboxamide as solvent. It is also possible to use mixtures of carboxamide and water containing up to 90% of water without requiring substantially more solvent than when carrying out the process in pure organic medium.

Accordingly, the present invention relates to a process for the preparation of 1,4-diamino-2,3-dicyanoanthraquinone by reacting diaminoanthraquinones, or salts thereof, of the formula

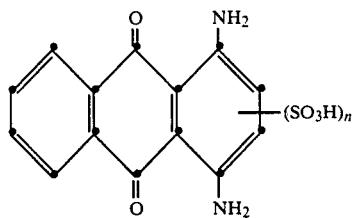

wherein n is 0, 1 or 2, with a compound that donates cyanide ions, in the presence of an oxidising agent, which process comprises using as solvent a mixture of a carboxamide, an N-alkylcarboxamide or a lactam and water, which mixture contains more than 10% by weight of water.

This process has the material advantage that the starting diaminoanthraquinone can be used as moist filter cake and does not have to be dried beforehand. In addition, carboxamides, e.g. acetamide, is degraded relatively easily by micro-organisms, so that when using mixtures of solvents containing c. 50% of water and more, these can be led direct into the wastewater after working up, thus rendering a troublesome and complicated regeneration of the solvent superfluous. Furthermore, it has been found that, surprisingly, the reaction in a mixture of carboxamide or lactam and water proceeds more rapidly than in an anhydrous carboxamide as sole solvent, whereby a higher space/time yield is obtained in the process of this invention. In addition, the preferred starting diaminoanthraquinonesulfonic acid and the cyanide are much more readily soluble in an aqueous-organic medium than in a pure organic one.

The starting diaminoanthraquinones of the indicated formula are known. Thus, for example, 1,4-diaminoanthraquinone-2-sulfonic acid is obtained by reacting 1-amino-4-bromoanthraquinone-2-sulfonic acid (bromamine acid) with ammonia under pressure (German patent specification Nos. 1 142 174 and 1 155 786).

If the process is carried out with diaminoanthraquinonemono- or -disulfonic acid as starting material, then not only the free acid but also the salts thereof, especially the alkali metal and ammonium salts, may be used. The preferred starting material is 1,4-diaminoanthraquinone-2-sulfonic acid.

The carboxamides employed as solvents in the process of this invention are preferably amides of monocarboxylic acids containing 1 to 6 carbon atoms in the chain. Typical examples are formamide, acetamide or propionamide. Also suitable are N-alkylated carboxamides, namely the N-monoalkylated amides, whereas N,N-dialkylcarboxamides have proved unsuitable. Examples of N-monoalkylated carboxamides are N-methylformamide and N-methylacetamide. Very good results are obtained, however, by using lactam/water mixtures as solvents. Suitable lactams are in particular those containing 5 to 7 members in the ring. Representative examples are: 2-pyrrolidone, 2-piperidone and ε-caprolactam. The preferred solvent is in particular acetamide, with 2-pyrrolidone being most preferred.

The process is carried out in a mixture of carboxamide or lactam and water. The amount of water, based on the mixture, is $>10\%$ by weight and may be up to 90% by weight. It is advantageous to use a mixture of carboxamide or lactam and water that contains 10 to 60% by weight of water.

The amount of water-containing solvent employed depends essentially on the solubility of the starting material. It is convenient to use an amount of solvent sufficient to dissolve the starting material completely. In general, 4 to 10 parts of water-containing carboxamide or lactam/water mixture are used per 1 part of diaminoanthraquinone or diaminoanthraquinonesulfonic acid.

The compounds employed as cyanide ion donors are preferably alkali metal and alkaline earth metal cyanides, for example sodium cyanide, potassium cyanide or magnesium cyanide. Further suitable cyanide ion donors are ammonium cyanide, hydrocyanic acid, and cyanhydrins of aldehydes and ketones. Sodium cyanide and potassium cyanide are preferred. The cyanide ion donor is advantageously used in an amount of 2 to 10 moles per mole of starting compound.

The process is carried out in the presence of an oxidising agent. Inorganic as well as organic oxidising agents are suitable, for example oxygen, nitriles, nitrates, bromates, persulfates, hydrogen peroxide, organic peracids such as peracetic acid, and also aromatic nitro compounds such as nitrobenzene, m-nitrobenzenesulfonic acid and salts thereof, or nitrobenzoic acid. Among these oxidising agents, nitrobenzene and m-nitrobenzenesulfonic acid are preferred.

Depending on the starting material, the reaction temperature is in the range from 40° to 150° C., advantageously from 60° to 100° C.

It has proved useful to add an acid acceptor to the reaction mixture, e.g. an alkali metal salt or alkaline earth metal salt of a weak acid. Examples of such acid acceptors are: sodium carbonate, potassium carbonate, sodium bicarbonate, sodium acetate, calcium carbonate or aqueous ammonia solution or ammonium bicarbonate. Besides inorganic compounds, organic bases are also suitable, for example mono-, di- or trialkylamines containing a $C_2$-$C_8$alkyl radical which may be interrupted by oxygen atoms, for example butylamine, triethylamine or tris(dioxa-3,6-heptyl)amine, or those alkylamines whose alkyl moieties are substituted e.g. by hydroxyl or alkoxy groups. It is preferred to use sodium carbonate, sodium bicarbonate, aqueous ammonia and/or mono-, di- or trialkylamines. If only ammonia is used as base, then the reaction is advantageously carried out under pressure.

The reaction can be readily monitored by thin-layer chromatography and is complete after 2 to 5 hours. Working up is relatively easy, as the diaminodicyanoanthraquinone is more sparingly soluble in the carboxamide or lactam/water mixture employed in the process of this invention than the starting compound and can therefore be readily isolated, e.g. by filtration or centrifugation. The process of the invention affords in good yield a diaminodicyanoanthraquinone which can be further processed direct to anthraquinoid disperse dyes.

The proces normally comprises charging the reactor with the 1,4-diaminoanthraquinone or the 1,4-diaminoanthraquinonesulfonic acid in a water-containing carboxamide, for example in a mixture of acetamide/water or lactam/water, e.g. a mixture of pyrrolidone/water containing 20 to 50% by weight of water, at room temperature, then adding an acid acceptor such as sodium crbonate or sodium bicarbonate and/or a tertiary amine, and finally adding the oxidising agent, for example m-nitrobenzenesulfonic acid and the cyanide, e.g. sodium cyanide. Before adding the acid acceptor, the pH of the solution is conveniently made neutral or weakly basic with aqueous ammonia. The reaction is complete after c. 30 minutes to 4 hours at a temperature of c. 80° C., and the precipitated product is isolated by filtration, washed with a small amount of water and/or methanol or ethanol, and subsequently dried. The desired product is obtained by this process in a yield of over 90%.

If 1,4-diaminoanthraquinone-2-sulfonic acid is used as starting material, it can be prepared in a prior reaction step from bromamine acid, as mentioned at the outset, by treatment with ammonia, in the presence of a copper salt, in the same solvent, and reacted to diaminodicyanoanthraquinone utilising the same reaction vessel and without isolation of the intermediate.

The following Examples will serve to illustrate the invention. Parts and percentages are by weight. TLC plates, silica gel 60 F-254 (Merck), are used for analysis of the product by thin-layer chromatography; the eluant is a 19:1 mixture of toluene/dioxane.

EXAMPLE 1

14.8 parts of 1,4-diaminoanthraquinone-2-sulfonic acid (86.1%) are added at 60° C. to a mixture of 18 parts of water and 72 parts of acetamide. Then 0.8 part of tris(dioxa-3,6-heptyl)amine, 0.8 part of sodium carbonate, 4.0 parts of m-nitrobenzenesulfonic acid and 15 parts parts of sodium cyanide are added in succession and the reaction mixture is stirred for 4 hours at a temperature of 80° C. The precipitate is filtered warm with suction, washed with warm water and with a small amount of methanol and dried in vacuo at 60° C., affording 12.0 parts of crude product. According to analysis, the 1,4-diamino-2,3-dicyanoanthraquinone is obtained in 89.3% purity, corresponding to a yield of 92.7% of theory. $R_f$=0.54.

EXAMPLE 2

The procedure of Example 1 is repeated, using a solvent mixture consisting of 45 parts of acetamide and 45 parts of water. 12.37 parts of product are isolated. According to analysis, the 1,4-diamino-2,3-dicyanoanthraquinone is obtained in 87.5% purity, corresponding to a yield of 93.7% of theory. $R_f$=0.54.

EXAMPLE 3

The procedure of Example 1 is repeated, using a solvent mixture consisting of 75 parts of formamide and 75 parts of water. 13.35 parts of product are isolated. According to analysis, the 1,4-diamino-2,3-dicyanoanthraquinone is obtained in 76.2% purity, corresponding to a yield of 88.1% of theory. $R_F$=0.54. About 5% of theory of product remains in the filtrate.

EXAMPLE 4

22.8 parts of 1,4-diaminoanthraquinone-2-sulfonic acid (78.1%) are added at room temperature to a mixture of 53 parts of 2-pyrrolidone and 52 parts of water. The pH of the solution is adjusted to 7.5–8 with 5 parts of 24% aqueous ammonia solution. Then 2 parts of ammonium bicarbonate, 6.4 parts of 3-nitrobenzene-1-sulfonic acid, sodium salt, and 9 parts of sodium cyanide are added in succession. The reaction mixture is then heated for 4 hours to 88° C., with stirring. The precipitate is filtered warm with suction, washed with warm 25% aqueous 2-pyrrolidone and then with hot water, and dried at 50° C. in vacuo, affording 14.9 parts of 95.5% 1,4-diamino-2,3-dicyanoanthraquinone, corresponding to a yield of 88.3% of theory. $R_f$=0.54.

EXAMPLE 5

The procedure of Example 4 is repeated, using a solvent mixture consisting of 60 parts of 2-piperidone and 40 parts of water. 15.2 parts of product are isolated. According to analysis, the 1,4-diamino-2,3-dicyanoanthraquinone is obtained in 93.0% purity, corresponding to a yield of 87.7% of theory. $R_f$=0.54.

EXAMPLE 6

65.2 parts of 1,4-diaminoanthraquinone-2-sulfonic acid (78.1%) are added at room temperature to a mixture of 180 parts of N-methylacetamide and 180 parts of water. The pH of the solution is adjusted to 7.5–8 with 15 parts of 24% aqueous ammonia solution. Then 18.2 parts of 3-nitrobenzene-1-sulfonic acid, sodium salt, and 25.5 parts of sodium cyanide are added in succession. The reaction mixture is then stirred for 4 hours at 75° C. The precipitate is filtered warm with suction and washed with hot water, and dried at 55° C. in vacuo, affording 47.6 parts of 91.1% 1,4-diamino-2,3-dicyanoathraquinone, corresponding to a yield of 94.1% of theory. $R_f=0.54$.

EXAMPLE 7

The procedure of Example 6 is repeated, using a solvent mixture consisting of 180 parts pf propionamide and 180 parts of water. 48.2 parts of 90.5% product are isolated, corresponding to a yield of 94.6% of theory. $R_f=0.54$.

What is claimed is:

1. A process for the preparation of 1,4-diamino-2,3-dicyanoanthraquinone by reacting a diaminoanthraquinone, or a salt, thereof, of the formula

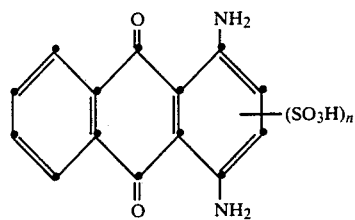

wherein n is 0, 1 or 2, with a compound which denotes cyanide ions, in the presence of an oxidising agent, which comprises using as solvent a mixture of a carboxamide, an N-alkylated carboxamide or a lactam and water, which mixture contains more than 10% and up to 90% by weight of water the reaction temperature being from 40° to 150° C.

2. A process according to claim 1, wherein the water-containing, optionally N-alkylated carboxamide employed is an amide of a monocarboxylic acid containing 1 to 6 carbon atoms in the chain.

3. A process according to claim 2, which comprises using a mixture of acetamide/water as solvent.

4. A process according to claim 1, which comprises using a water-containing lactam containing 5 to 7 members in the ring as solvent.

5. A process according to claim 4, which comprises using a mixture of 2-pyrrolidone and water as solvent.

6. A process according to claim 1, which comprises using as solvent a mixture of carboxamide or lactam and water, said mixture containing 10 to 60% by weight of water.

7. A process according to claim 1, which comprises using sodium cyanide or potassium cyanide as compound which donates cyanide ions.

8. A process according to claim 1, which comprises using nitrobenzene or m-nitrobenzenesulfonic acid as oxidising agent.

9. A process according to claim 1, wherein an acid acceptor, preferably sodium carbonate, sodium bicarbonate, aqueous ammonia and/or a mono-, di- or trialkylamine is added to the reaction mixture.

10. A process according to claim 1, wherein 1,4-diaminoanthraquinone-2-sulfonic acid is used as starting material.

* * * * *